United States Patent [19]

Benedetti

[11] Patent Number: 4,699,782

[45] Date of Patent: Oct. 13, 1987

[54] GALENICAL FORMULATION OF TOLOXATONE

[75] Inventor: Margherita S. Benedetti, Paris, France

[73] Assignee: Delalande S.A., Courbevoie, France

[21] Appl. No.: 518,519

[22] Filed: Jul. 29, 1983

[51] Int. Cl.$^4$ ............................................. A61K 31/78
[52] U.S. Cl. ..................................................... 424/81
[58] Field of Search ......................................... 424/81

[56] References Cited

PUBLICATIONS

The Lancet, Oct. 26, 1983 edition, pp. 849 through 851.
Remington's Pharmaceutical Sciences, 16th Edition, pp. 1040 through 1042.
Physician's Desk Reference, pp. 1374, 1375, 1512, 1513, 1684 and 1685.
Vidal, pp. 778, 873, 879 and 1357.

*Primary Examiner*—Stanley J. Friedman
*Attorney, Agent, or Firm*—Flynn, Thiel, boutell & Tanis

[57] ABSTRACT

A new formulation for the oral administration of Toloxatone, an anti-depressant, contains 400 to 600 mg of Toloxatone per unit dose. Such a high Toloxatone content is possible due to the discovery that Toloxatone is competitive with Tyramine towards the A form of a monomine oxidase, and thus does not cause hypertensive crisis. The anti-depressant composition of this invention can therefore be administered to the patient even when Tyramine is present in the patient's system.

5 Claims, 1 Drawing Figure

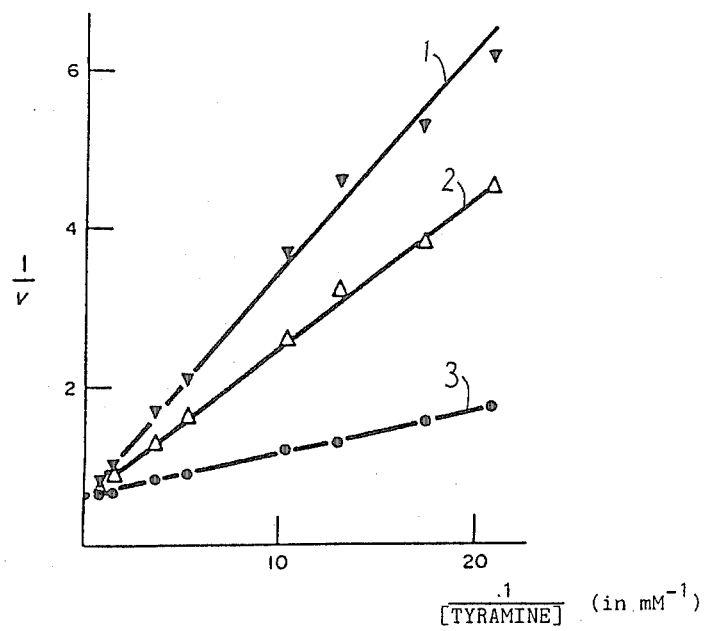

GALENICAL FORMULATION OF TOLOXATONE

The present invention relates to a new galenical formulation for the oral administration of a known antidepressant, Toloxatone.

U.S. Pat. No. 29,607 describes the therapeutical use, more especially as an anti-depressant, of a series of compounds administrable orally in the form of tablets or capsules containing from 50 to 250 mg of active ingredient.

One of these compounds, the one of code number 69276 (international common name: Toloxatone) has been clinically studied and these studies confirm its antidepressive activity in man (M. Martin, 1973, Un nouvel antidépresseur le MD 69276—L'information psychiatrique, vol. 49, No. 10, p. 1023-1025; G. Ferrey—Etude en double aveugle de la Toloxatone versus Clomipramine chez des malades déprimés, rapport d'expertise du 30.3.83; S. J. Dencker and A. Nagy, A pilot study of a new selective MAO inhibitor: toloxatone, accepted for publication in Nord. Psykiatr. Tidsskr.).

These clinical studies have in particular shown that the efficient daily dose of Toloxatone for men, for an antidepressive action, is between 800 mg and 1000 mg. According to the dosages indicated in U.S. Pat. No. 29,607, this daily efficient dose requires the administration of at least 4 to 5 tablets or capsules per day. This administration, imposing severe constraints (for checking the amounts taken) on patients and nursing staff in a hospital environment becomes practically impossible and intolerable for external patients, especially for long term treatments.

It is recognized that depressive conditions result from a reduction, in the central nervous system, of certain neurotransmitters such as noradrenaline (NA) and serotonine (5-HT). Antidepressants act by raising the rates of said neurotransmitters by means of two principal mechanisms:
- inhibition of the "re-uptake" of said neurotransmitters,
- inhibition of monoamine oxidase.

A thorough biochemical study of Toloxatone has shown that its antidepressive action is due to the inhibition of monoamine oxidase (MAO) and particularly of A form of MAO (J. P. Kan et al., J. Pharm. Pharmacol., 1978, 30, 190-93; P. E. Keane et al., J. Pharm. Pharmacol., 1979, 31, 752-54).

The A form of MAO is the form of the enzyme responsible for the degradation of NA and 5-HT.

All the known inhibitors of MAO (MAOI) used up to now are irreversible and non-specific inhibitors of MAO, i.e. they inhibit both the A form and the B form of the enzyme and often other enzymatic systems. They require the greatest care in use for they cause extremely dangerous secondary effects, particularly the "cheese effect" characterized by a hypertensive crisis which may cause death, this effect appearing after ingestion of certain tyramine rich foods (Blackwell, Lancet, 1963, p. 849-51; Goldberg, J. Am. J. Med. Assoc., 1964, 190, p. 456-62; Young, Austr. J. Pharm. Sci., 1981, 10, p. 1-8).

The secondary effects of MAOIs seriously limit then the use thereof, and although it was known that Toloxatone was a reversible MAO-A inhibitor and had a weak affinity for the A form of MAO, nevertheless there was every reason to fear as well such limitations in its use, especially since it requires a relatively high daily dose (800 to 1000 mg/day) to be efficient. The low affinity of Toloxatone for MAO-A is demonstrated by the value of the inhibition constants (Ki) of intestinal MAO-A: 3.4 $\mu$M and cerebral MAO-A: 2.0 $\mu$M. Determination of these Ki constants is effected by using respectively homogenates of the proximal part of the intestine of rats (in the ratio 1/16 by weight/volume, in the presence of 100 mM of a phosphate buffer (at pH 167 7.4) or mitochondrias of rat brain (prepared according to the method described by Gray and Whittaker in J. Anat., 1962, 96, 79), by taking NA as substrate, according to the method described by Harada et al. in Biochem. Pharmacol. 1979, 28, 2465).

BRIEF DESCRIPTION OF DRAWING

The drawing is a graph showing the relationship between the reciprocal of the tyramine concentration and the reciprocol of the oxidation rate.

Now, thorough biochemical studies have revealed that Toloxatone is competitive with Tyramine towards the form A of MAO.

The competitive character of the Toloxatone and Tyramine interaction with respect to MAO-A is shown by the curves of the drawing which show the relationship existing between the inverse of the Tyramine concentration (1/[TYRAMINE]) and the inverse of the oxidization rate (1/V).

The rat intestine homogenates are incubated with $10^{-7}$ moles of 1-deprenyl for 20 min at 37° C. (to selectively inhibit the activity of MAO-B). They are then incubated with distilled water or with Toloxatone (5 $\mu$M or 10 $\mu$M) for 5 minutes at 37° C. before the addition of Tyramine ($^{14}$C marked Tyramine).

After incubation, the products of the reaction are extracted by means of an aprotic solvent or a mixture of aprotic solvents and the radioactivity is counted by liquid scintillation. In the drawing, the curve 1 presents the results obtained using 10 $\mu$M of Toloxatone, the curve 2 presents the results obtained using 5 $\mu$M of Toloxatone and the curve 3 presents the results obtained using distilled water.

This competitivity property of Toloxatone is of prime importance; it means that Toloxatone may be readily displaced from its fixing sites on the enzyme by Tyramine which may therefore be de-amined and will cause no hypertensive effects.

The joint administration in man of toloxatone (1 g/day for 7 days) and Tyramine administered intravenously or orally has been sought. This study has shown that Toloxatone does not potentialize the pressure effect of Tyramine which means that Toloxatone should not cause "cheese effect".

This study was made by using the following methods.

A. Tyramine administered intravenously: (study carried out on five healthy volunteers of masculine sex). Each subject receives 1 g of Toloxatone or placebo per day for 7 days. At the end of the treatment 1 hour after administration of Toloxatone, Tyramine was administered by intravenous perfusion at does of 1, 2, 4, 8, 16, 32 and 64 mc.g/kg/minute. The perfusion rate is doubled every five minutes until a dose of 64 mc.g/kg/minute is reached. The heart beat rate is recorded for the 5th minute of each perfusion and the arterial pressure is taken twice during the same time. It is noted that the variations of the index:

(systolic arterial pressure)/(heart beat rate)

(which takes into account both the increase of the pressure and the slowing down of the heart beat rate caused by Tyramine) are practically identical after administration of the placebo and after administration of Toloxatone.

B. Tyramine administered orally (study carried out blind on four healthy volunteers for 3 weeks).

The first and last weeks, the subjects receive 1 g per day of Toloxatone. The intermediate week, the Toloxatone was replaced by placebo.

The sixth and seventh days of the first week, the subjects receive, on an empty stomach, respectively 100 and 200 mg of Tyramine, two hours after administration of Toloxatone.

The sixth day of the intermediate week (under placebo), the subjects receive a dose of 400 mg of Tyramine and the following day a dose of 800 mg.

The sixth day of the 3rd week each subject receives 400 mg of Tyramine.

The effect of oral absorption of Tyramine is always calculated by the index:

$$(\text{systolic arterial pressure})/(\text{heart beat rate})$$

It was seen that the variations of the index recorded with 200 mg of Tyramine under Toloxatone are practically identical to those recorded with 400 mg of Tyramine under placebo and those recorded with 400 mg of Tyramine under Toloxatone are less than those recorded with 800 mg of Tyramine under placebo. The effects noted have no clinical significance.

As comparsion, we will mention that with conventional MAOIs (Phenelzine, Clorgyline) hypertensive effects were recorded from a dose of 6 mg of Tyramine [Davis et coll. Lacet, 1,172–75, (1978); Lader et coll. Psychopharmacoligia, 18, 118–23, (1970)].

We will also mention here, by way of comparison, the amounts of Tyramine present in some foods known to contain some:

gruyère cheese: 516 μg/g
emmenthal cheese: 225 μg/g

[see Drug Interaction, Biological Council of D. G. Grahame-Smith, p. 171, (1977)].

Consequently, Toloxatone appears as an antidepressant acting by selective inhibition of the A form of MAO, but which, quite unexpectedly, does not cause the secondary effects met with the known MAOIs and more especially does not cause the "cheese effect". It follows that it may be used with complete safety and without food restriction, orally in the form of unit doses (such as tablets or capsules) containing amounts of active ingredient far greater than the limits (50–250 mg) advocated in U.S. Pat. No. Re. 29,607, which limits could not up to present be exceeded without risk, precisely because of the secondary effects of MAOIs.

Thus, the present invention proposes a new galenical formulation of Toloxatone, formed more precisely by unit doses adapted for oral administration, such as tablets or capsules, containing 400 to 600 mg of active ingredient in association with a pharmaceutically acceptable vehicle. This dosage allows efficient doses to be rapidly reached (800–1000 mg/day) split up into a maximum of two or three sub-doses, while imposing no particular constraint on the patients (or nursing staff) required by the posology given in U.S. Pat. No. 29,607.

By way of non limiting example, the tablets of the invention may contain 65 to 75% of active ingredient, 2 to 4% of polyvinylpyrrolidinone (P.V.P.), 7 to 15% of starch, 8 to 15% of lactose, 3 to 6% of sodic carboxymethylstarch and 0.75 to 1.5% of magnesium stearate. Thus, for example, the corresponding formulation of a tablet containing 400 mg of Toloxatone would be:

Toloxatone: 400 mg
P.V.P.: 17 mg
Starch: 57 mg
Lactose: 68 mg
Sodic carboxymethylstarch: 22 mg
Magnesium stearate: 6 mg and the formulation of a tablet, containing 600 mg of Toloxatone would be:

Toloxatone: 600 mg
P.V.P.: 25 mg
Starch: 85 mg
Lactose: 100 mg
Sodic carboxymethylstarch: 32 mg
Magnesium stearate: 8 mg

I claim:

1. An anti-depressant composition of the form of a solid unit dose for oral administration to a human subject suffering from depression, consisting essentially of 400 to 600 mg of Toloxatone, and the balance is essentially a solid pharmaceutically acceptable vehicle.

2. A composition as claimed in claim 1, wherein said composition is in the form of tablets containing 400 mg of Toloxatone.

3. A tablet consisting of 65–75 wt. % Toloxatone, 2–4 wt. % polyvinylpyrrolidinone, 7–15 wt. % starch, 8–15 wt. % lactose, 3–6 wt. % sodium carboxymethylstarch and 0.75–1.5 wt. % magnesium stearate, which tablet contains 400 to 600 mg of Toloxatone.

4. A method of treating a patient suffering from depression which comprises administering to said patient not more than three of the unit doses claimed in claim 1, per day.

5. A method of treating a patient suffering from depression which comprises administering to said patient not more than three of the tablets claimed in claim 3, per day.

* * * * *